United States Patent [19]

Beck et al.

[11] Patent Number: 4,698,357

[45] Date of Patent: Oct. 6, 1987

[54] 2,4-DICHLORO-5-NITRO-THIAZOLE

[75] Inventors: Gunther Beck; Paul Reinecke, both of Leverkusen; Wilfried Paulus; Hans-Georg Schmitt, both of Krefeld, all of Fed. Rep. of Germany

[73] Assignee: Bayer Aktiengesellschaft, Leverkusen, Fed. Rep. of Germany

[21] Appl. No.: 863,638

[22] Filed: May 15, 1986

[30] Foreign Application Priority Data

May 23, 1985 [DE] Fed. Rep. of Germany ....... 3518520

[51] Int. Cl.$^4$ .................... C07D 277/58; A01N 43/78
[52] U.S. Cl. ..................................... 514/370; 548/193
[58] Field of Search ......................... 548/193; 514/370

[56] References Cited

PUBLICATIONS

Annales Pharmaceutiques Francaises, 1964, Max Robba & Robert C. Moreau, "Synthese ... Candida Albicans", pp. 202–210.

Chemical Abstracts 61:3087f, vol. 61, 3087–3088.

Soc. Chim. France, 1962, pp. 1735–1738.

Primary Examiner—Robert Gerstl
Attorney, Agent, or Firm—Sprung Horn Kramer & Woods

[57] ABSTRACT

The compound 2,4-dichloro-5-nitro-thiazole of the formula

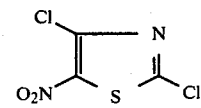

is microbicidally active.

3 Claims, No Drawings

2,4-DICHLORO-5-NITRO-THIAZOLE

The invention relates to 2,4-dichloro-5-nitrothiazole, which is new, a process for its preparation, and its use as a microbicide.

It is already known that certain dithiocarbamates, such as, for example, zinc ethylene-1,2-bis-dithiocarbamate, possess fungicidal properties (see, for example, R. Wegler "Chemie der Pflanzenschutz- und Schädlingsbekämpfungsmittel" (Chemistry of plant protection agents and pest-combating agents), Springer Verlag Berlin, Heidelberg, New York 1970, volume 2, page 65 et seq.).

However, the action of these compounds is not always completely satisfactory in all fields of use, particularly when small amounts and concentrations are used.

2,4-Dichloro-5-nitro-thiazole, which is new, and of the formula (I)

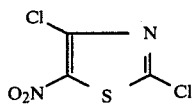

has been found.

2,4-Dichloro-5-nitro-thiazole of the formula (I)

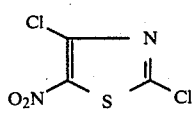

is obtained when 2,4-dichloro-thiazole of the formula (II)

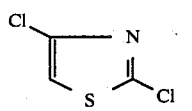

is reacted with customary nitrating agents.

2,4-Dichloro-5-nitro-thiazole, which is new, possesses powerful microbicidal properties.

Surprisingly, the 2,4-dichloro-5-nitro-thiazole according to the invention has a substantially more powerful microbicidal, especially fungicidal, action than zinc ethylene-1,2-bis-dithio-carbamate, which is known from the prior art and is a similar compound in terms of its action.

If 2,4-dichlorothiazole and nitric acid are used as starting materials, the course of the reaction can be represented by the following equation:

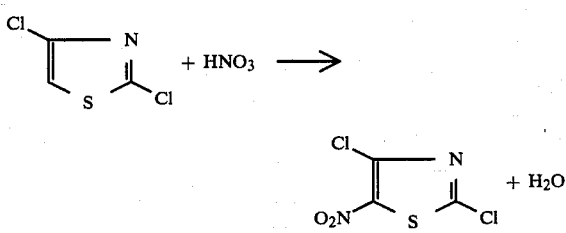

2,4-Dichlorothiazole of the formula (II) which is required as a starting material for carrying out the process according to the invention is known (see, for example, Bull. Soc. chim. France 1962, 1735), as are the required nitrating agents, which are generally known inorganic compounds.

Suitable nitrating agents for carrying out the process according to the invention are all generally customary nitrating agents, such as, for example, nitric acid or mixtures of nitric acid and sulphuric acid.

In carrying out the process according to the invention, the reaction temperature can be varied within a relatively wide range. In general, the reaction is carried out at $-30°$ to $+60°$ C., preferably at $0°$ to $+30°$ C.

In carrying out the process, it is possible, as stated above, to effect nitration with the customary nitrating agents, such as, for example, mixtures of nitric acid and sulphuric acid (for example those consisting of 33% of $HNO_3$ and 67% of $H_2SO_4$) or with nitric acid alone (for example 98% strength nitric acid).

Nitration is advantageously carried out with an excess of nitric acid, which may be in general between 2 and 20 mols of nitric acid per mol of 2,4-dichlorothiazole. Specifically, the process is carried out as follows: the 2,4-dichloro-thiazole is added in portions to the nitrating agent in the stated temperature range, while stirring and, if required, while cooling, after which the mixture is discharged onto several times, for example 5-10 times, the amount of ice-water, and the precipitated crystalline 2,4-dichloro-5-nitro-thiazole is filtered off.

The active compound according to the invention exhibits a powerful microbicidal action and can be employed in practice for combating undesired microorganisms. The active compound is suitable for use as a microbicide in plant protection, especially as a fungicide, or can be employed in material protection for protecting technical materials.

Fungicidal agents, for example in plant protection, are employed for combating Plasmodiophoromycetes Oomycetes, Chytridiomycetes, Zygomycetes, Ascomycetes, Basidiomycetes and Deuteromycetes.

Bactericidal agents are employed, for example, in plant protection for combating Pseudomonadaceae, Rhizobioaceae, Enterobacteriaceae, Corynebacteriaceae and Streptomycetaceae.

Some causative organisms of fungal and bacterial diseases included under the abovementioned main headings are mentioned below as non-limiting examples:

Xanthomonas species, such as, for example, *Xanthomonas campestris* pv. *oryzae;* Pseudomonas species, such as, for example, *Pseudomonas syringae* pv. *lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaeraleucotricha;* Venturia species, such as, for example, *Venturia inaequalis;* Pyrenophora species, such as, for example, *Pyrenophora teres* or *P. graminea;* (Conidial form: Drechslera, Synonym: Helminthosporium); Cochliobolus species, such as, for example, *Cochliobolus sativus;* (Conidial form: Drechslera, Synonym: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *PYricularia oryzae;* Fusarium species, such as, for example, *Fusarium culmorum;* Botrytis species; such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* Pseudocercosporella species, such as, for example, *Pseudocercosporella herpotrichoides.*

The good toleration, by plants, of the active compound, at the concentrations required for combating plant diseases, permits treatment of above-ground parts of plants, of vegetative propagation stock and seeds, and of the soil.

As a microbicidal agent, the active compound according to the invention can be used with particularly good success for combating cereal diseases, for example those caused by *Cochliobolus sativus* and *Drechslera graminea.* The good fungicidal action against Fusarium on cereals and against Pyricularia on rice may also be mentioned. In addition, when used appropriately, the compound according to the invention also has a good action as a leaf insecticide and a good acaricidal action, as well as an action against hygiene pests and pests in stored materials.

The active compound can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example, by mixing the active compound with extenders, that is, liquid solvents, liquefied gases under pressure and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or form-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in the formulations as a mixture with other known active compounds, such as fungicides, insecticides, acaricides and herbicides, as well as in mixtures with fertilizers and growth regulators.

The active compound can be used as such or in the form of its formulations or the use forms prepared therefrom, such as ready-to-use solutions, emulsifiable concentrates, emulsions, foams, suspensions, wettable powders, pastes soluble powders, dusting agents, and granules. They are used in the customary manner, for example by watering, spraying, atomizing, scattering, dusting, foaming, brushing on etc. It is also possible to apply the active compound by the ultra low volume method or to inject the active compound preparation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 kg per kilogram of seed, preferably 0.01 to 10 g are generally required.

For the treatment of soil, active compound concentrations of 0.00001 to 0.1% by weight, preferably 0.0001 to 0.02%, are required at the place of action.

According to the invention, technical materials are inanimate materials which have been prepared for use in industry. For example, technical materials which are to be protected, by active compounds according to the invention, from microbial change or destruction can be adhesives, glues, paper and cardboard, textiles, leather, wood, paints and plastic articles, cooling lubricants and other materials which may be attacked or destroyed by microorganisms. Within the scope of the materials to be protected, it is also possible to mention parts of production plants, for example cooling water circulations, which can be adversely affected by multiplication of microorganisms. Within the scope of the present invention, adhesives, glues, papers and cardboards, leather, wood, paints, cooling lubricants and cooling circulations may preferably be mentioned as technical materials.

For example, bacteria, fungi, yeasts, algae and slime organisms may be mentioned as microorganisms which can cause degradation or modification of the technical materials. The active compounds according to the invention preferably act against fungi, in particular moulds, wood-discolouring and wood-destroying fungi (Basidiomycetes), and against slime organisms and algae.

Microorganisms of the following genera may be mentioned by way of example:
Alternaria, such as *Alternaria tenuis,*
Aspergillus, such as *Aspergillus niger,*
Chaetomium, such as *Chaetomium globosum,*
Coniophora, such as *Coniophora puteana,*
Lentinus, such as *Lentinus tigrinus,*
Penicillium, such as *Penicillium glaucum,*
Polyporus, such as *Polyporus versicolor,*
Aureobasidium, such as *Zureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on the field of use, an active compound according to the invention can be converted into the customary formulations, such as solutions, emulsions, suspensions, powders, pastes and granules.

These can be prepared in a manner which is in itself known, for example by mixing the active compound with an extender which consists of a liquid solvent and/or solid carriers, if appropriate with the use of surface-active agents, such as emulsifiers and/or dispersants, and, in the case of the use of water as an extender, organic solvents, such as alcohols, can, if appropriate, be used as auxiliaries.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, and halogenated hydrocarbons, such as 1,2-dichloroethane.

Microbicidal agents contain the active compound in general in an amount of from 1 to 95%, preferably from 10 to 75%.

The concentrations in which the active compound according to the invention is used depend on the type and occurrence of the microorganisms to be combated, and on the composition of the material to be protected. The optimum amount used can be determined by test series. In general, the concentrations used are in the range from 0.001 to 5% by weight, preferably from 0.05 to 1.0% by weight, based on the material to be protected.

The active compound according to the invention can also be present as a mixture with other known active compounds. For example, the following active compounds may be mentioned: benzyl alcohol mono(poly)-hemiformal and other formaldehyde-donating compounds, benzimidazolyl methylcarbamates, tetramethylthiuram disulphide, zinc salts of dialkyl dithiocarbamates, 2,4,5,6-tetrachloroisophthalonitrile, thiazolyl-benzimidazole, mercaptobenzothiazole, organo-tin compounds, methylenebisthiocyanate and phenol derivatives, such as 2-phenylphenol, 2,2'-dihydroxy-5,5'-dichloro-diphenylmethane and 3-methyl-4-chlorophenol.

PREPARATION EXAMPLES

Example 1

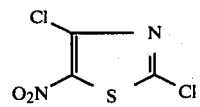

400 g (2.6 mols) of 2,4-dichloro-thiazole are introduced in portions, in the course of one hour at between 15° and 20° C., into 2 liters of 98% strength nitric acid (density=1.51; about 47 mols), while stirring and cooling. Thereafter, the mixture is discharged in portions onto about 20 kg of ice/water, while stirring thoroughly and the precipitate formed is filtered off under suction while still cold, washed neutral with water and dried between clay plates. 494 g (95.5% of theory) of 2,4-dichloro-5-nitro-thiazole are obtained in this manner. Melting point of a sample recrystallized from low-boiling petroleum ether: 38°–39° C.

Example 2

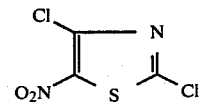

120 g (0.78 mol) of 2,4-dichloro-thiazole are introduced in portions, in the course of one hour at between 15° and 20° C., into 300 ml of "mixed acid" (density=1.81; consists of 33% by weight of nitric acid and 67% by weight of sulphuric acid; about 2.8 mols of nitric acid). Thereafter, the mixture is discharged onto 3 kg of ice and worked up as in Example 1. The yield is 134.3 g (86.5% of theory) of 2,4-dichloro-5-nitro-thiazole.

USE EXAMPLES

In the use examples below, the compound listed below is employed as a comparative substance:

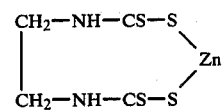

Zinc ethylene-1,2-bis-dithiocarbamate

Example A

*Cochliobolus sativus* test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus.* The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown by the compound according to the invention.

Example B

*Drechslera graminea* test (barley)/seed treatment (syn. *Helminthosporium gramineum*)

The active compound is used as dry dressings. These are prepared by extending the active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown by the compound according to the invention.

Example C

Action against bacteria

The active compound according to the invention, in various concentrations, is added to an agar which contains broth as the nutrient medium. Thereafter, the nutrient medium is infected with different test organisms in each case, and the infected medium is kept at 28° C. and 60–70% relative atmospheric humidity for 2 weeks. The MIC is the lowest concentration of active compound at which the microbe species used exhibits no growth at all. The compound according to the invention has good actions.

Example D

To demonstrate the effectiveness against fungi, the minimum inhibitory concentrations (MIC) of the active compound according to the invention are determined:

The active compound according to the invention, in various concentrations, is added to an agar which is prepared from beer-wort and peptone. After the agar has solidified, contamination with pure cultures of various test organisms is effected. After storage for 2 weeks at 28° C. and 60 to 70% relative atmospheric humidity, the MIC is determined. The MIC is the lowest concentration of active compound at which the microbe species used exhibits no growth at all.

The compound has good actions.

It will be understood that the specification and examples are illustrative but not limitative of the present invention and that other embodiments within the spirit and scope of the invention will suggest themselves to those skilled in the art.

What is claimed is:

1. 2,4-Dichloro-5-nitro-thiazole of the formula

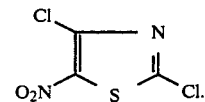

2. A fungicidal or bactericidal composition comprising a fungicidally or bactericidally effective amount of a compound according to claim 1 and a diluent.

3. A method of combating fungi or bacteria which comprises applying thereto or to a habitat thereof a fungicidally or bactericidally effective amount of a compound according to claim 1.

* * * * *